(12) United States Patent
Tsai

(10) Patent No.: US 6,296,837 B1
(45) Date of Patent: Oct. 2, 2001

(54) FRAGRANT FINGERNAIL POLISH

(76) Inventor: Ting-Chun Tsai, No. 11, Lane 26, Tzehsin Rd, Sanhsia Town, Taipei County (TW)

(*) Notice: Subject to any disclaimer, the term of this patent is extended or adjusted under 35 U.S.C. 154(b) by 0 days.

(21) Appl. No.: 09/524,604

(22) Filed: Mar. 14, 2000

(51) Int. Cl.$^7$ .............................. A61K 6/00; A61K 7/00; A61K 7/04
(52) U.S. Cl. ............................. 424/61; 424/401
(58) Field of Search .................................. 424/61, 401

(56) References Cited

U.S. PATENT DOCUMENTS 5,424,061 * 6/1995 Pappas et al. ..................... 424/61

* cited by examiner

Primary Examiner—Thurman K. Page
Assistant Examiner—S. Howard
(74) Attorney, Agent, or Firm—Rosenberg, Klein & Lee

(57) ABSTRACT

A fragrant fingernail polish composed of 35.5 wt % ethyl solvent, 20 wt % butyl solvent, 12 wt % acetone, 16.5 wt % cellulose acetate butyrate, 10 wt % acrylic resin, 0.5 wt % whitening-preventive agent, 4.4 wt % artificial pearl powder, 0.55 wt % dye of desired base color, and 0.55 wt % perfume.

1 Claim, 3 Drawing Sheets

FRAGRANT FINGERNAIL POLISH

BACKGROUND OF THE INVENTION

The present invention relates to a fingernail polish, and more particularly to a fragrant fingernail polish, which has a delightful fragrance and, can be used as an ornamental coating for application to a variety of writing materials, personal items, electric and electronic appliances (telephones and cellular telephones).

Before going to the outside, every woman usually will use beauty products to make the skin, fingernails, hair and face beautiful, and perfume to spray over the skin for emitting a pleasant smell. Because perfume is volatile, the pleasant smell of perfume cannot last for long. Therefore, a woman may have to spray perfume daily or several times a day. Further, a variety of fingernail polishes are commercially available, however these fingernail polishes simply polish fingernails without emitting a pleasant smell.

SUMMARY OF THE INVENTION

It is one object of the present invention to provide a fingernail polish, which emits a pleasant smell for long. It is another object of the present invention to provide a fragrant fingernail polish, which can be used as a fragrant apparatus coating for application to any of a variety of writing materials, personal items, electric and electronic appliances. According to the present invention, the fragrant fingernail polish comprises 35.5 wt % ethyl solvent, 20 wt % butyl solvent, 12 wt % acetone, 16.5 wt % cellulose acetate butyrate, 10 wt % acrylic resin, 0.5 wt % whitening-preventive agent, 4.4 wt % artificial pearl powder, 0.55 wt % dye of desired base color, and 0.55 wt % perfume.

DETAILED DESCRIPTION OF THE PREFERRED EMBODIMENT

Figure 1:
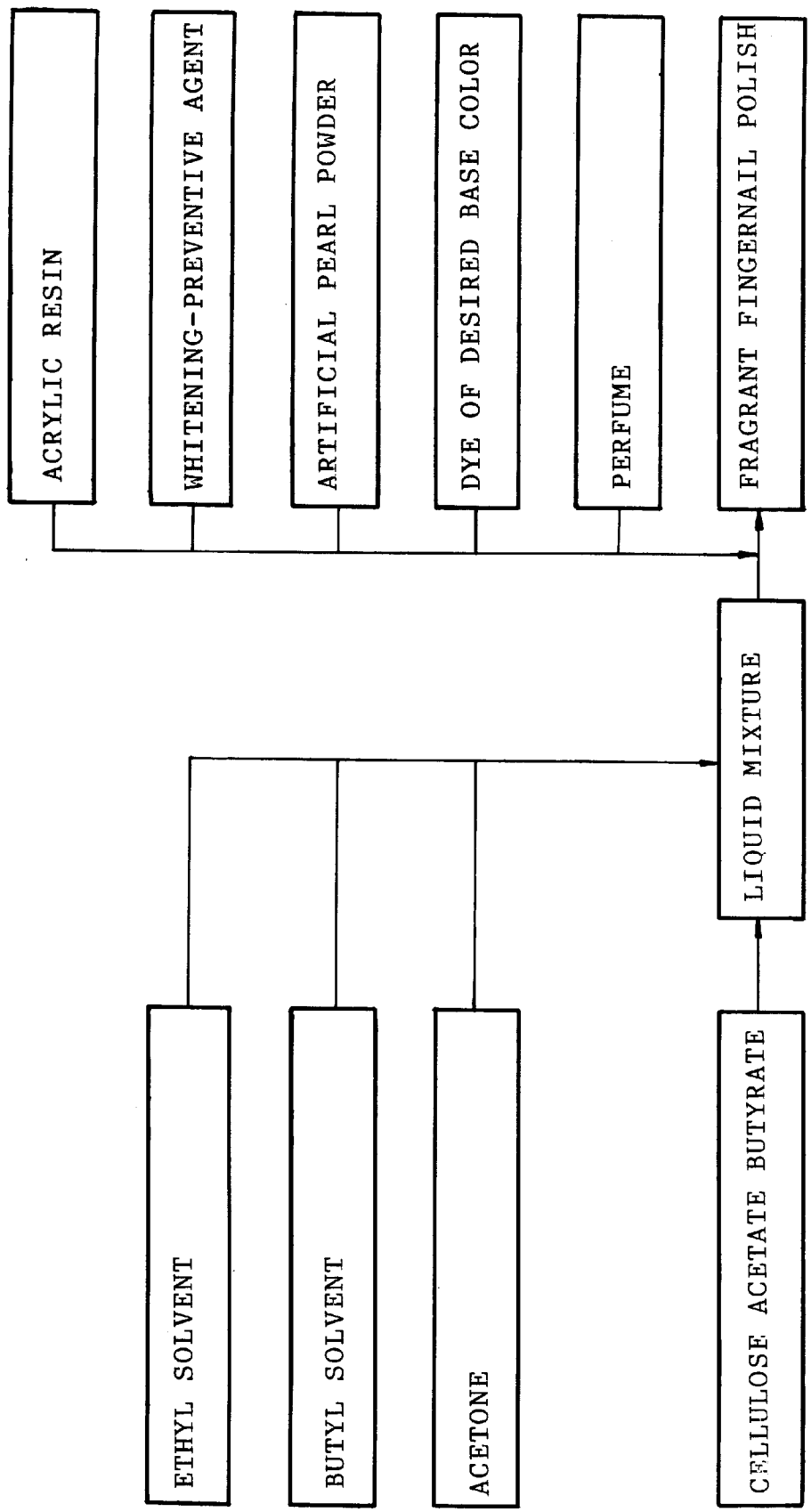
FIG. 1 is a block diagram explaining the fragrant fingernail polish production flow according to the present invention.

Referring to FIG. 1, a fragrant fingernail polish according to the present invention is obtained by: mixing 35.5 wt % ethyl solvent, 20 wt % butyl solvent, 12 wt % acetone and 16.5 wt % cellulose acetate butyrate into a liquid mixture, and then adding to the liquid mixture 10 wt % acrylic resin, 0.5 wt % whitening-preventive agent, 4.4 wt % artificial pearl powder, 0.55 wt % dye of desired base color, and 0.55 wt % perfume.

Figure 3:
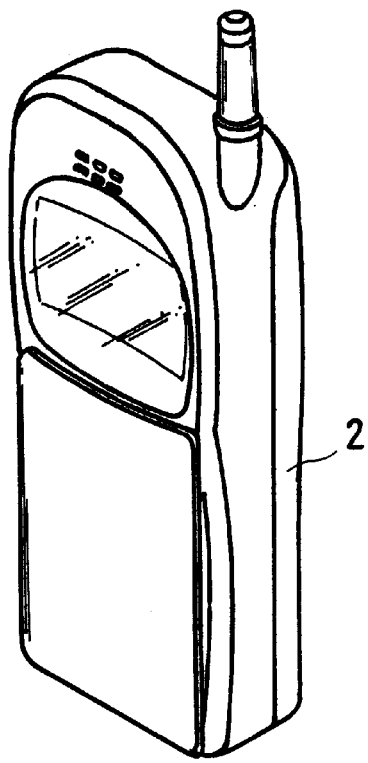
FIG. 3 shows the fragrant fingernail polish coated on a cellular telephone according to the present invention.
Figure 2:
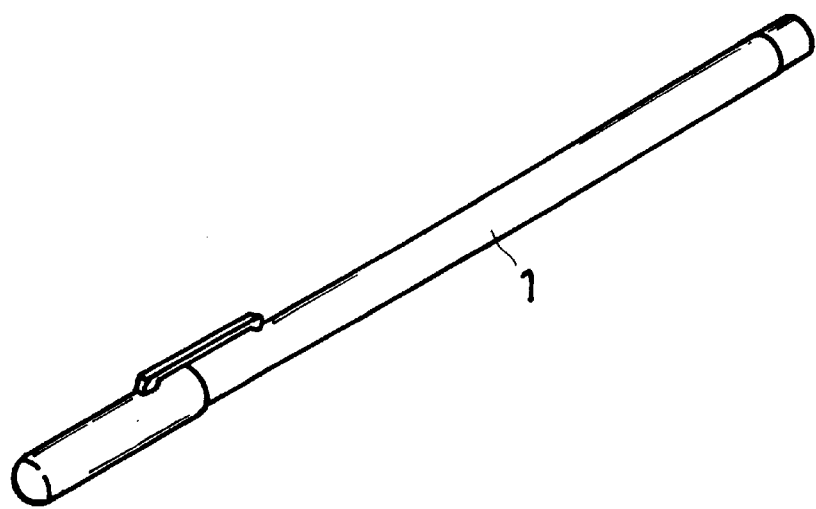
FIG. 2 shows the fingernail polish coated on a pen according to the present invention.
Figure 5:
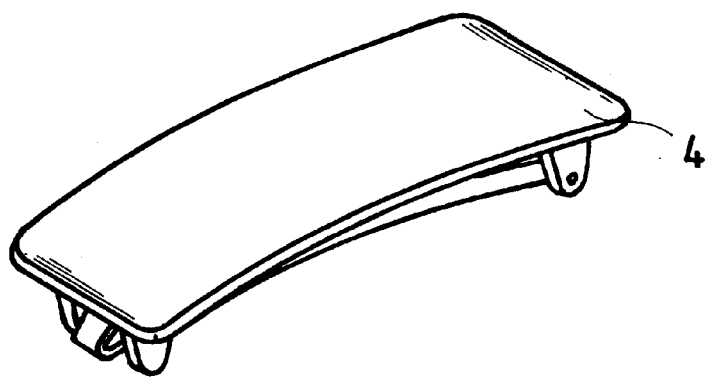
FIG. 5 shows the fragrant fingernail polish coated on a barrette according to the present invention.
Figure 4:
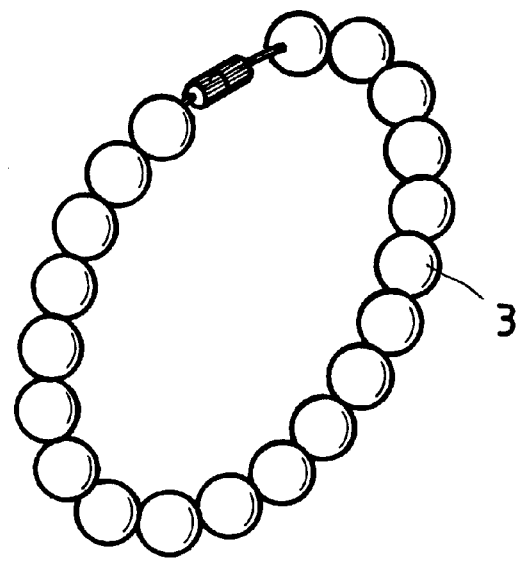
FIG. 4 shows the fragrant fingernail polish coated on an artificial pearl necklace according to the present invention.

When the fragrant finger polish is applied to fingernails, it makes the fingernails beautiful, and emits a pleasant smell for long. The fragrant finger polish can also be used as a fragrant coating for any of a variety of writing materials, personal items, electric and electronic appliances. For example, the fragrant fingernail polish can be coated on a pen 1 (see FIG. 2), a cellular telephone 2 (see FIG. 3), an artificial pearl necklace 3 (see FIG. 4), a barrette 4 (see FIG. 5).

Further, a fragrant fingernail polish can be made having any of a variety of colors and any of a variety of pleasant smells. By changing the kind of the dye and the perfume during the production, a fragrant fingernail polish of the desired color and smell is obtained.

What the invention claimed is:

1. A fragrant fingernail polish comprising 35.5 wt % ethyl solvent, 20 wt % butyl solvent, 12 wt % acetone, 16.5 wt % cellulose acetate butyrate, 10 wt % acrylic resin, 0.5 wt % whitening-preventive agent, 4.4 wt % artificial pearl powder, 0.55 wt % dye of desired base color, and 0.55 wt % perfume.

* * * * *